(12) United States Patent
Chin et al.

(10) Patent No.: US 6,470,277 B1
(45) Date of Patent: Oct. 22, 2002

(54) TECHNIQUES FOR FACILITATING IDENTIFICATION OF CANDIDATE GENES

(75) Inventors: Daniel J. Chin, Foster City; Donna Hendrix, Berkeley; Oliver Zhao, Daly City, all of CA (US)

(73) Assignee: AGY Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 09/628,202

(22) Filed: Jul. 28, 2000

Related U.S. Application Data

(63) Continuation of application No. 09/365,587, filed on Jul. 30, 1999.

(51) Int. Cl.[7] .......................... G06F 17/30; G06F 7/00; G06F 17/00; G01N 31/00; G01N 33/48
(52) U.S. Cl. ........................... 702/19; 707/3; 707/6; 707/7; 707/10; 702/19; 702/27; 706/45; 706/47
(58) Field of Search .............................. 707/10, 104, 3, 707/6, 7; 702/27, 19; 706/45, 47

(56) References Cited

U.S. PATENT DOCUMENTS

| | | | |
|---|---|---|---|
| 5,571,639 | A | 11/1996 | Hubbell et al. |
| 5,593,839 | A | 1/1997 | Hubbell et al. |
| 5,633,161 | A | 5/1997 | Shyjan |
| 5,807,522 | A | 9/1998 | Brown et al. |
| 5,840,484 | A | 11/1998 | Seilhamer et al. |
| 5,942,399 | A | * 8/1999 | Hillman et al. |
| 5,953,727 | A | 9/1999 | Maslyn et al. |
| 6,023,659 | A | 2/2000 | Seilhamer et al. |
| 6,189,013 | B1 | * 2/2001 | Maslyn et al. |

FOREIGN PATENT DOCUMENTS

| | | |
|---|---|---|
| WO | WO 97/15690 | 5/1997 |
| WO | WO 97/47763 | 12/1997 |
| WO | WO 99/01581 | 1/1999 |
| WO | WO 99/05574 | 2/1999 |
| WO | WO 99/05591 | 2/1999 |
| WO | WO 9915626 | 4/1999 |

OTHER PUBLICATIONS

Nevill–Manning et al., "Highly specific protein sequence motifs for genome analysis," Proc. Natl. Acad. Sci. USA, vol. 95, No. 11, pp. 5865–5871, 1998.*

Anton J. Enright, Ioannis Iliopoulous, Nikos C. Kyrpides & Christos A. Ouzounis, "Protein Interaction Maps For Complete Genomes Based on Gene Fusion Elements", Nature, Letters to Nature, vol. 402, Nov. 4, 1999, pp. 86–90.

Edward M. Marcotte, Matteo Pellegrini, Michael J. Thompson, Todd O. Yeates & David Eisenberg, "A Combined Algorithm For Genome–Wide Prediction of Protein Function," Nature, Letters to Nature, vol. 402, Nov. 4, 1999, pp. 83–86.

Andrej Sali, "Functional Links Between Proteins,"Nature, News and Views, vol. 402, Nov. 4, 1999, pp. 23, 25–26.

Hua et al., "Construction of a modular yeast two hybrid cDNA library from human EST clones for the human genome protein linkage map," Gene, 1998, vol. 215, No. 1, pp. 143–152.

Ingram et al., "Developing mouse models of aging: a consideration of strain differences in age–related behavioral and neural parameters," Neuralbiology of Aging, 1999, vol. 20, No. 2, pp. 137–145.

* cited by examiner

Primary Examiner—John S. Brusca
Assistant Examiner—Young Kim
(74) Attorney, Agent, or Firm—Townsend and Townsend and Crew LLP

(57) ABSTRACT

Techniques for facilitating the identification of candidate genes from a plurality of DNA sequences. According to an embodiment of the present invention, techniques are provided for extracting and integrating information from various information sources and results of various analyses, and storing the integrated information in a form which is conducive to identification of candidate genes. The stored information may include results of a homology search for the plurality of DNA sequences, annotative information for the plurality of DNA sequences indicating the biochemical functions and physiological roles of the plurality of DNA sequences, gene expression profile data for the plurality of DNA sequences describing behavioral patterns of the plurality of DNA sequences, results from clustering the plurality of DNA sequences based on time course data as described by the gene expression profile data, and other information.

11 Claims, 9 Drawing Sheets

| Score | Journal | Score | Journal |
|---|---|---|---|
| 100 | Nature | 80 | Brain |
| 100 | Science | 80 | Journal of Physiology |
| 97 | Cell | 80 | Molecular and Cellular Endocrinology |
| 96 | Neuron | 80 | Molecular and Cellular Neurosciences |
| 96 | Nature Structural Biology | 78 | Genome Research |
| 95 | Nature Cell Biology | 78 | Journal of Clinical Epidemiology |
| 95 | Nature Genetics | 78 | Pharmacology |
| 95 | Nature Medicine | 75 | Genomics |
| 95 | Nature Neuroscience | 75 | Journal of Cellular Biochemistry |
| 94 | Journal of Structural Biology | 75 | Journal of Investigative Dermatology |
| 94 | New England Journal of Medicine | 75 | Journal of Medical Genetics |
| 92 | Journal of Biological Chemistry | 75 | Journal of Medical Virology |
| 92 | Journal of Lipid Research | 75 | Journal of Psychiatric Research |
| 92 | Journal of Molecular Biology | 75 | Nitric Oxide |
| 92 | Neuroscience | 75 | Toxicology |
| 91 | Journal of Bacteriology | 74 | Brain and Development |
| 91 | Journal of Cell Biology | 73 | Cancer Immunology, Immunotherapy |
| 91 | Journal of Immunology | 70 | Brain Injury |
| 91 | Journal of Neurochemistry | 70 | Cytogenetics and Cell Genetics |
| 90 | Biochemistry | 70 | Glia |
| 90 | Bioinformatics | 70 | Journal of Biotechnology |
| 90 | Immunology | 70 | Obesity Research |
| 90 | Journal of Clinical Investigation | 69 | Immunopharmacology |
| 90 | Journal of Internal Medicine | 68 | Cellular Signaling |
| 90 | Journal of Medicinal Chemistry | 68 | immunology and Cell Biology |
| 90 | Journal of Membrane Biology | 68 | Stem Cells |
| 90 | Journal of Neuroscience | 68 | Stroke |
| 90 | Journal of Virology | 68 | Synapse |
| 90 | Molecular Microbiology | 67 | Immunology Letters |
| 89 | Cell Biology | 65 | Cell Motility and the Cytoskeleton |
| 89 | Genetics | 65 | Gene |
| 89 | Journal of Experimental Medicine | 65 | Hormone Research |
| 89 | Journal of Neurobiology | 65 | Journal of Cognitive Neuroscience |
| 89 | Neurology | 65 | Journal of the Neurological Sciences |
| 88 | Infection and Immunity | 65 | Pharmacological Research |
| 87 | Journal of Neuroendocrinology | 63 | American Journal of Physiology |
| 87 | Journal of Neuroimmunology | 62 | American Journal of Medicine |
| 87 | Journal of Neurology | 62 | Journal of Comparative Neurology |
| 87 | Neuroendocrinology | 60 | American Journal of Human Genetics |
| 86 | Neuroscience Letters | 60 | Cell Proliferation |
| 85 | Development | 55 | Journal of Affective Disorders |
| 85 | Proceedings National Academy of Sciences | 50 | DNA and Cell Biology |
| 85 | Immunogenetics | 45 | Anesthesiology |
| 85 | Journal of Cell Science | 41 | Biochemical Journal |
| 85 | Journal of Infectious Diseases | 40 | Anesthesia and Analgesia |
| 85 | Journal of Neurophysiology | 40 | Biochemical Pharmacology |
| 85 | Molecular Pharmacology | 40 | Cell Biochemistry and Function |
| 85 | Molecular and Cellular Biology | 40 | Cell and Tissue Research |
| 84 | Brain Research | 40 | Cerebral Cortex |
| 84 | Developmental Biology | 40 | Experimental Cell Research |
| 84 | Developmental Neuroscience | 40 | Histochemistry and Cell Biology |
| 84 | Molecular Biology of the Cell | 35 | Journal of Dermatological Science |
| 83 | Cancer | 20 | Chemistry and Biology |
| 82 | Analytical Biochemistry | 20 | Genes, Chromosomes and Cancer |
| 82 | Journal of Endocrinology | 20 | International Journal of Biochemistry and Cell Biology |
| 82 | journal of Experimental Biology | 20 | International Journal of Developmental Neuroscience |
| 82 | Journal of histochemistry and Cytochemistry | 10 | Archives of Biochemistry and Biophysics |
| 82 | Journal of Molecular Endocrinology | 10 | International Journal of Antimicrobial Agents |
| 82 | Molecular Immunology | 10 | International Journal of Cancer |
| 82 | Natural Immunity | 10 | International Journal of Experimental Pathology |
| 82 | Nucleic Acids Research | 10 | Journal of Antisense Research |

*Fig. 9*

TECHNIQUES FOR FACILITATING IDENTIFICATION OF CANDIDATE GENES

CROSS-REFERENCES TO RELATED APPLICATIONS

This application also claims priority from and is a continuation-in-part application of non-provisional U.S. patent application Ser. No. 09/365,587, entitled "SYSTEM AND METHOD FOR IDENTIFYING CRITICAL REGULATED GENES" filed Jul. 30, 1999, the entire contents of which are herein incorporated by reference in their entirety for all purposes.

COPYRIGHT NOTICE

A portion of the disclosure of this patent document contains material which is subject to copyright protection. The copyright owner has no objection to the xerographic reproduction by anyone of the patent document or the patent disclosure in exactly the form it appears in the U.S. Patent and Trademark Office patent file or records, but otherwise reserves all copyright rights whatsoever.

BACKGROUND OF THE INVENTION

The present invention relates generally to the field of bioinformatics, and more particularly to techniques for facilitating the identification of candidate genes.

With recent advances in the identification of expressed sequence tags (ESTs) and the sequencing of the human genome, a number of researchers are now directing their efforts towards analyzing the data from the genome maps and sequences. A significant portion of this research is being directed towards identifying genes which might trigger, prevent, ameliorate, or somehow affect a variety of diseases or physiological states. Such genes are commonly referred to as "candidate" genes.

The identification of candidate genes is critical to entities such as drug companies who may use the information related to the candidate genes to identify better drug targets in the drug development process. The early identification of candidate genes could reduce the number of potential therapeutics moving through a company's clinical testing pipeline, significantly reducing overall costs and reducing the time taken by the company to market the drugs.

However, conventional techniques do not facilitate easy identification of candidate genes. This is due to the enormous amount of information being generated by the researchers, and the lack of adequate tools to organize the information in a manner which facilitates analysis of the information. For example, techniques such as parallel expression and analysis using cDNA arrays, as described in U.S. Pat. No. 5,807,522, and synthetic DNA array technology, as described in U.S. Pat. Nos. 5,593,839 and 5,571,639, have been developed to study large scale gene expression profiles (e.g. time-courses of a disease process or comparisons between an altered physiologic or metabolic state with an untreated biological sample). Databases and algorithms have also been developed to analyze the results of the above-mentioned array technologies. Public databases of metabolic, genetic and physiological pathways of yeast (e.g., Munich Information Center for Protein Sequences (MIPS)) and some mammalian genes (e.g., Kyoto Encyclopedia of Genes and Genomes (KEGG)) have been developed largely from the published literature of many traditional low-throughput experimental studies. However, the information provided by the various sources of information identified above and other sources has not been integrated in a coherent manner conducive to identification of candidate genes.

Based on the foregoing, there is a need for techniques which can facilitate the identification of candidate genes. It is desirable that these techniques be able to correlate various types of information and store it in a format which can be easily accessed or queried by researchers interested in identifying candidate genes.

SUMMARY OF THE INVENTION

The present invention discusses techniques for facilitating identification of candidate genes from a plurality of DNA sequences. According to an aspect of the present invention, techniques are provided for extracting and integrating information from various information sources and results of various analyses, and storing the integrated information in a form which facilitates identification of candidate genes.

According to an embodiment, the present invention accesses results of a homology search for the plurality of DNA sequences, annotative information for the plurality of DNA sequences indicating the biochemical functions and physiological roles of the plurality of DNA sequences, gene expression profile data for the plurality of DNA sequences describing behavioral patterns of the plurality of DNA sequences, results from clustering the plurality of DNA sequences based on the behavioral patterns of the plurality of DNA sequences as described by the gene expression profile data, and other information. The information accessed by the present invention is stored in a format, e.g. a database, which facilitates identification of candidate genes.

According to another embodiment, the present invention receives queries identifying criteria for the candidate genes. In response to the queries, the present invention searching the database storing information for the plurality of DNA sequences to identify a set of DNA sequences which satisfy the query criteria. The set of DNA sequences are then output as a result of the query.

According to yet another embodiment of the present invention, a user may configuring a query identifying criteria for the candidate genes and communicate the query to a server storing information related to a plurality of DNA sequences. According to this embodiment, the information related to the plurality of DNA sequences may comprise results of a homology search for the plurality of DNA sequences, annotative information for the plurality of DNA sequences describing the biochemical functions and physiological roles of the plurality of DNA sequences, gene expression profile data for the plurality of DNA sequences describing behavioral patterns of the plurality of DNA sequences, results from clustering the plurality of DNA sequences based on the behavioral patterns of the plurality of DNA sequences as described by the gene expression profile data, and other information. In response to the query, the user receives a first set of DNA sequences which satisfy the criteria for the candidate genes identified in the query.

The invention will be better understood by reference to the following detailed description and the accompanying figures.

BRIEF DESCRIPTION OF THE DRAWINGS

FIG. 9 is an exemplary look-up table for general rankings of biomedical journals.

DESCRIPTION OF THE SPECIFIC EMBODIMENTS

The present invention discusses techniques for facilitating identification of candidate genes from a plurality of DNA sequences. According to an aspect of the present invention, techniques are provided for extracting and integrating information from various information sources and results of various analyses, and storing the integrated information in a form which facilitates identification of candidate genes.

As part of the analysis, an embodiment of the present invention analyzes and extracts information from homology searches performed on a plurality of DNA sequences. According to another aspect, the present invention extracts descriptive annotative information from various information stores about cDNA clones, which have been isolated on the basis of differential expression from various disease models or altered physiological states. According to another embodiment, the present invention extracts information about causally ordered (i.e. as defined by autoregression-based causality analysis) behavioral patterns of differentially expressed cDNAs from gene expression profile data. According to another embodiment, the present invention correlates the descriptive annotative information about cDNA clones with numerical experimental data on the behavior of the cDNAs extracted from, for example, the gene expression profiling data. According to another embodiment, the present invention integrates the information to provide a model to facilitate experimental testing of the candidate genes. The information extracted/obtained by the present invention is stored in a database. According to an embodiment of the present invention, users may query the information stored in the database to identify candidate genes.

Figure 1:
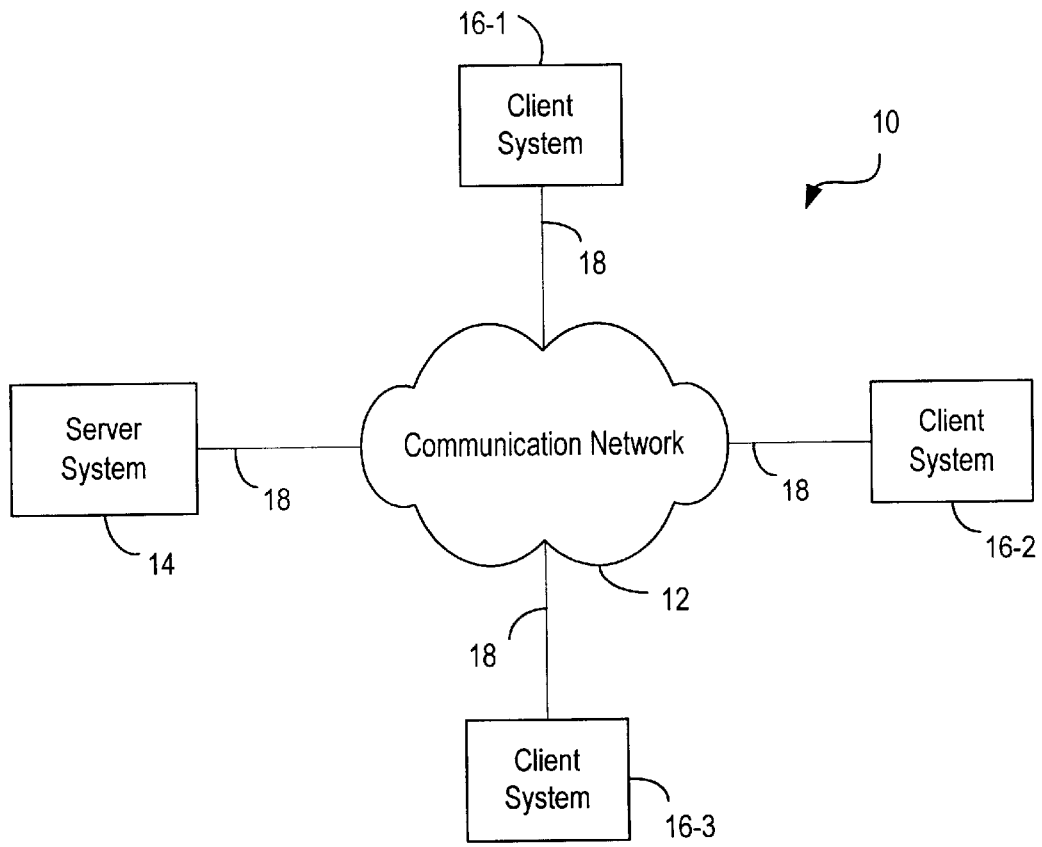
FIG. 1 is a simplified block diagram of a distributed computer network incorporating an embodiment of the present invention.

FIG. 1 is a simplified block diagram of a distributed computer network 10 incorporating an embodiment of the present invention. Computer network 10 includes a number of client systems 16-1, 16-2, and 16-3, and a server system 14 coupled to a communication network 12 via a plurality of communication links 18. Communication network 12 provides a mechanism for allowing the various components of distributed network 10 to communicate and exchange information with each other. Communication network 12 may itself be comprised of many interconnected computer systems and communication links. Communication links 18 may be hardwire links, optical links, satellite or other wireless communications links, wave propagation links, or any other mechanisms for communication of information. While in one embodiment, communication network 12 is the Internet, in other embodiments, communication network 12 may be any suitable computer network. Distributed computer network 10 depicted in FIG. 1 is merely illustrative of an embodiment incorporating the present invention and does not limit the scope of the invention as recited in the claims. One of ordinary skill in the art would recognize other variations, modifications, and alternatives. For example, more than one server system 14 may be coupled to communication network 12.

Client systems 16 typically request information from a server computer system which provides the information. For this reason, servers typically have more computing and storage capacity than client systems. However, a particular computer system may act as both as a client or a server depending on whether the computer system is requesting or providing information. Additionally, although the invention has been described using a client-server environment, it should be apparent that the invention may also be embodied in a stand-alone computer system.

According to the teachings of the present invention, server system 14 is responsible for obtaining and storing information for a plurality of DNA sequences in order to facilitate identification of candidate genes from the DNA sequences. Server system 14 may store the information in one or more databases accessible to server 14. These databases may be locally coupled to server 14 or may be distributed across distributed computer network 10 and accessed by server 14 via communication network 12.

Software modules executing on server system 14 are responsible for obtaining information from a plurality of information sources, and integrating and storing the information in a manner which facilitates identification of candidate genes. The information sources may include databases accessible to server system 14, results from various analyses, published sources of information such as magazine articles, etc., and other like information sources. Server 14 also provides services allowing users to select, access, retrieve, or query information stored by the server.

Server 14 is responsible for receiving information requests from client systems 16, performing processing required to satisfy the requests, and for forwarding the results corresponding to the requests back to the requesting client system. The processing required to satisfy the request may be performed by server 14 or may alternatively be delegated to other servers connected to communication network 12.

According to the teachings of the present invention, client systems 16 enable users to access and query information stored by server system 14. In a specific embodiment, a "web browser" application executing on a client system enables users to select, access, retrieve, or query information stored by server system 14. Examples of web browsers include the Internet Explorer browser program provided by Microsoft Corporation, and the Netscape Navigator browser provided by Netscape Corporation, and others.

Figure 2:
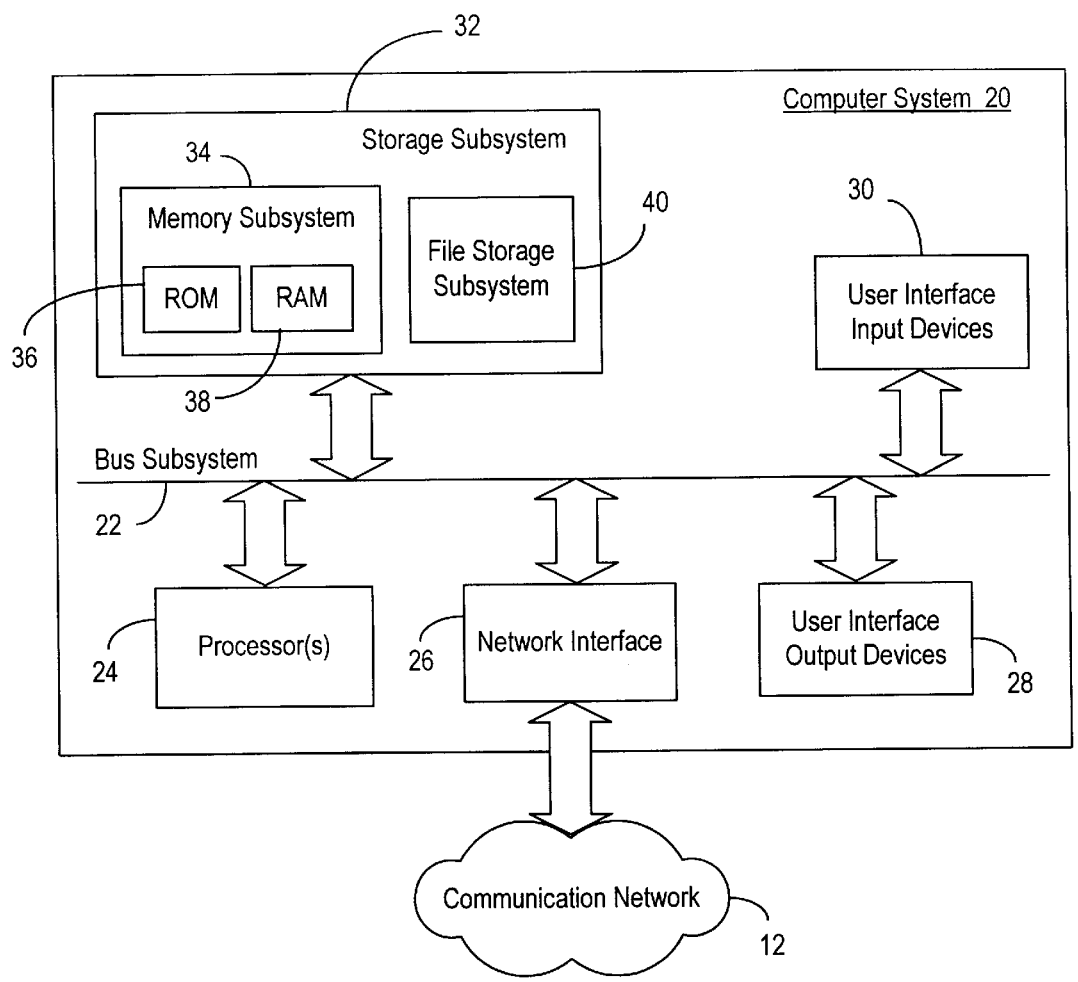
FIG. 2 is a simplified block diagram of a computer system according to an embodiment of the present invention.

FIG. 2 is a simplified block diagram of computer system 20 according to an embodiment of the present invention. Computer system 20 typically includes at least one processor 24 which communicates with a number of peripheral devices via bus subsystem 22. These peripheral devices typically include a storage subsystem 32, comprising a memory subsystem 34 and a file storage subsystem 40, user interface input devices 30, user interface output devices 28, and a network interface subsystem 26. The input and output devices allow user interaction with computer system 20. It should be apparent that the user may be a human user, a device, another computer, and the like. Network interface subsystem 26 provides an interface to outside networks, including an interface to communication network 12, and is coupled via communication network 12 to corresponding interface devices in other computer systems.

User interface input devices 30 may include a keyboard, pointing devices such as a mouse, trackball, touchpad, or graphics tablet, a scanner, a touchscreen incorporated into the display, audio input devices such as voice recognition systems, microphones, and other types of input devices. In general, use of the term "input device" is intended to include all possible types of devices and ways to input information into computer system 20 or onto computer network 12.

User interface output devices 28 may include a display subsystem, a printer, a fax machine, or non-visual displays such as audio output devices. The display subsystem may be a cathode ray tube (CRT), a flat-panel device such as a liquid crystal display (LCD), or a projection device. The display subsystem may also provide non-visual display such as via audio output devices. In general, use of the term "output device" is intended to include all possible types of devices and ways to output information from computer system 20 to a human or to another machine or computer system.

Storage subsystem 32 stores the basic programming and data constructs that provide the functionality of the various systems embodying the present invention. For example, the various modules implementing the functionality of the present invention may be stored in storage subsystem 32. These software modules are generally executed by processor 24. In a distributed environment, the software modules may be stored on a plurality of computer systems and executed by processors of the plurality of computer systems. Storage subsystem 32 also provides a repository for storing the various databases storing information according to the present invention. Storage subsystem 32 typically comprises memory subsystem 34 and file storage subsystem 40.

Memory subsystem 34 typically includes a number of memories including a main random access memory (RAM) 38 for storage of instructions and data during program execution and a read only memory (ROM) 36 in which fixed instructions are stored. File storage subsystem 40 provides persistent (non-volatile) storage for program and data files, and may include a hard disk drive, a floppy disk drive along with associated removable media, a Compact Digital Read Only Memory (CD-ROM) drive, an optical drive, removable media cartridges, and other like storage media. One or more of the drives may be located at remote locations on other connected computers at another site on communication network 12. Information stored according to the teachings of the present invention may also be stored by file storage subsystem 40.

Bus subsystem 22 provides a mechanism for letting the various components and subsystems of computer system 20 communicate with each other as intended. The various subsystems and components of computer system 20 need not be at he same physical location but may be distributed at various locations within distributed network 10. Although bus subsystem 22 is shown schematically as a single bus, alternate embodiments of the bus subsystem may utilize multiple busses.

Computer system 20 itself can be of varying types including a personal computer, a portable computer, a workstation, a computer terminal, a network computer, a television, a mainframe, or any other data processing system. Due to the ever-changing nature of computers and networks, the description of computer system 20 depicted in FIG. 2 is intended only as a specific example for purposes of illustrating the preferred embodiment of the present invention. Many other configurations of a computer system are possible having more or less components than the computer system depicted in FIG. 2. Client computer systems 16 and server computer systems 14 generally have the same configuration as shown in FIG. 2, with the server systems generally having more storage capacity and computing power than the client systems.

Figure 3:
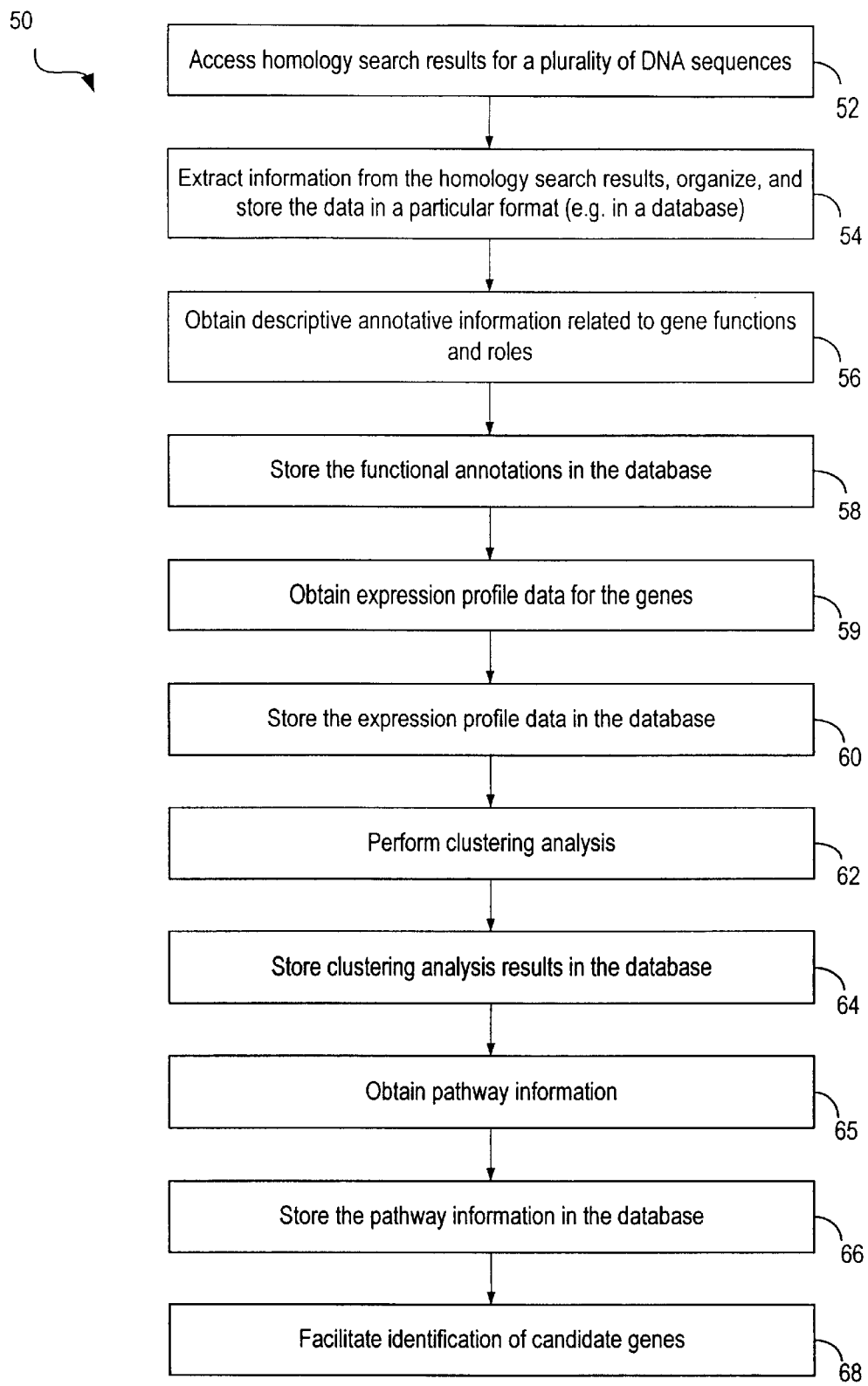
FIG. 3 is a simplified flowchart showing processing performed by an embodiment of the present invention to facilitate identification of candidate genes from a plurality of input DNA sequences.

FIG. 3 depicts a simplified flowchart 50 showing processing performed by an embodiment of the present invention to facilitate identification of candidate genes from a plurality of input DNA sequences. As shown in FIG. 3, processing is initiated when the server system 14 accesses results of a homology search from the plurality of input DNA sequences (step 52).

The DNA sequences which are input as queries to the homology search are generally complementary DNA (cDNA) sequences which have been synthesized using isolated messenger RNA (mRNA) sequences, which are the transcription products of expressed genes. The cDNA sequences are used as input sequences to the homology search analysis since cDNAs represent expressed genomic regions and are thus believed to identify parts of the genome with the most biological and medical significance.

As part of the homology search, DNA and protein sequence databases are searched to find sequences which are related to the input or query DNA sequences. For example, given a set of differentially expressed query cDNA sequences corresponding to the mRNA of their cognate genes, a homology search identifies known, similar and unknown genes. A homology search is generally performed by using computer-implemented search algorithms to compare the query cDNA sequences with sequence information stored in a plurality of databases accessible via a communication network, for example, the Internet. Examples of such algorithms include the Basic Local Alignment Search Tool (BLAST) algorithm, the PSI-blast algorithm, the Smith-Waterman algorithm, the Hidden Markov Model (HMM) algorithm, and other like algorithms. For example, a "blastn" program utilizing the BLAST algorithm may be used to search the Genbank database for homologs of the query cDNA sequences. According to an embodiment of the homology search, the query cDNA sequences may be grouped as "known," "unknown," or "similar" sequences. "Known" cDNA sequences include sequences with substantial sequence identity to existing sequence entries in a sequence database, such as the GenBank database. "Unknown" cDNA sequences include sequences similar to existing sequence entries in a sequence database but lacking functional annotation, or those sequences with no matching sequences in existing sequence databases. "Similar" cDNA sequences include sequences for which no matches are found in the sequence database, but which exhibit similarity, as defined below, to existing entries in sequence databases.

Two or more sequences may exhibit "substantial sequence identity" if the sequences have at least 70%, preferably 80%, most preferably 90%, 95%, 98% or 99% nucleotide or amino acid residue identity, when compared and aligned for maximum correspondence, as measured using a particular sequence comparison algorithm or by using visual inspection.

Several different sequence comparison techniques may be used. According to a first technique, two sequences (amino acid or nucleotide) can be compared over their full-length (e.g. the length of the shorter of the two, if they are of substantially different lengths) or over sub-sequences of at least 200, about 200, about 500 or about 1000 contiguous nucleotides or at least about 40, about 50, or about 100 contiguous amino acid residues. According to an embodiment of the present invention, a query cDNA sequence may qualified as a "known" gene if the query DNA sequence meets the following stringent criteria: (1) a sequence length greater than 200 nucleotides with greater than or equal to 80% identity over 70% of the query sequence length with an E-value (a probability value of a match occurring if the sequence were randomized) of less than 1e-50; and (2) for the predicted amino acid homology, greater than or equal to 80% identity for a segment length greater than 50 amino acids and an E-value of less than 1e-20. Sequences that meet either, but not both, the DNA or protein sequence criteria may be grouped as "similar" genes after examination of the respective DNA or protein alignments.

For sequence comparison, typically one sequence acts as a reference sequence, to which test sequences are compared. When using a sequence comparison algorithm, test and reference sequences are input to a computer, subsequence coordinates are designated, if necessary and sequence algorithm program parameters are designated. The sequence comparison algorithm then calculates the percent sequence identity for the test sequence(s) relative to the reference sequence, based on the designated program parameters.

As stated above, a plurality of homology search algorithms may be used to determine optimal alignment of sequences. These include the local homology algorithm of Smith & Waterman, Adv. Appl. Math. 2:482 (1981), the homology alignment algorithm of Needleman & Wunsch, J. Mol. Biol., 48:443 (1970), the similarity method of Pearson & Lipman, Proc. Natl. Acad. Sci. USA 85:2444 (1988), the PSI-Blast homology algorithm of Altschul et al., Nucleic Acids Res. 25:3389–402 (1997), the computerized implementations of algorithms GAP, BESTFIT, FASTA, and TFASTA included in the Wisconsin Genetics Software Package, Genetics Computer Group, 575 Science Dr., Madison, Wis.), by Hidden Markov Models (HMM, Durbin, Eddy, Krogh & Mitchison, Cambridge University Press, 1998), or EMotif/EMatrix to identify sequence motifs (Nevill-Manning, Wu, & Brutlag, Proc Natl. Acad. Sci USA. 1998 May 26;95(11):5865–71), or by visual inspection (see generally Ausubel et al., supra). Each of the above identified algorithms and the references are herein incorporated by reference in its entirety for all purposes. These algorithms are well known to one of ordinary skill in the art of molecular biology and bioinformatics. When using any of the aforementioned algorithms, the default parameters for "Window", gap penalty, etc., are used. Practitioners of the art molecular biology with average skill will recognize these parameters as: (a) the "window" is typically a 9, 10 or 11 nucleotide word length of sequence over which the homology is determined; and (b) gap penalty is a scoring value to prevent large gaps from occurring in reported alignments.

The BLAST algorithm is well suited for determining percent sequence identity and sequence similarity. The BLAST algorithm is described in Altschul et al., J Mol. 215:403–410, (1990), the entire contents of which are herein incorporated by reference for all purposes. Several software programs incorporating the BLAST algorithm are publicly available through the National Center for Biotechnology Information (NCBI) (http://www.ncbi.nlm.nih.gov/). These programs include the blastp, blastn, blastx, tblastn, tblastx, and PSI-blast software programs. Due to codon wobble or species differences, more informative homologies can be found by comparing the predicted protein sequence of a DNA query sequence to a protein sequence database. For this task, the Smith-Waterman or PSI-BLAST algorithms may be used. Similarly, for weak homologs, functional domains of proteins may be discerned by Smith-Waterman, HMM or Emotif algorithms. Software for performing HMM and Smith-Waterman analysis can be obtained from a variety of public sources (e.g. http://hmmer.wustl.edu/; http://www.stanford.edu/~sntaylor/bioc218/final.htm#Appendix) and/or from vendors that sell accelerated computer hardware to rapidly process large batches of sequences (e.g. Paracel, Pasadena, Calif. or Time-Logic, Reno, Nev.). Software for EMotif/Ematrix can be obtained from sources such as the Brutlag Bioinformatics Group, Stanford University, Stanford, Calif..

The BLAST heuristic search algorithm is optimized for speed and searches sequence databases accessible to server 14 for optimal local alignments to the input query DNA sequences. Databases which may be searched using the BLAST programs include the SWISS-PROT protein sequence database, GenBank database, the Genome Sequence database (GSDB), the European Molecular Biology Laboratory (EMBL) Nucleotide Sequence database, the DNA Database of Japan (DDBJ), and other like databases.

The BLAST algorithm identifies high scoring sequence pairs (HSPs) by identifying short words of length "W" in the query cDNA sequence, which either match or satisfy some positive-value threshold score "T" when aligned with a word of the same length in a database sequence. "T" is referred to as the neighborhood word score threshold (Altschul et al, supra). An "X" parameter is a positive integer representing the maximum permissible decay of the cumulative segment score during word hit extension. These initial neighborhood word hits act as seeds for initiating searches to find longer HSPs containing them. The word hits are then extended in both directions along each sequence for as far as the cumulative alignment score can be increased. Extension of the word hits in each direction are halted when the cumulative alignment score goes to zero or below, due to the accumulation of one or more negative-scoring residue alignments, or when the end of either sequence is reached. The BLAST algorithm parameters "W", "T", and "X" determine the sensitivity and speed of the alignment. Accordingly, the stringency of a BLAST search can be adjusted by appropriately setting the search parameters. However, if the search parameters are too loose, an excessive amount of biologically questionable "hits" may be returned. The BLAST program uses as defaults a wordlength (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N-4, and a comparison of both strands. Typically, the default parameters can yield from zero to scores of likely homologs for the input query DNA sequences.

In addition to calculating percent sequence identity, the BLAST algorithm also performs a statistical analysis of the similarity between two sequences (see, e.g. Karlin & Altschul, Proc. Natl. Acad. Sci. USA 90:5873–5787 (1993)). One measure of similarity provided by the BLAST algorithm is the smallest sum probability (P(N) or E-value as an expected value), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about 0.001, and most preferably less than about 0.0001.

A further indication that two nucleic acid sequences or polypeptides are substantially identical is that the polypeptide encoded by the first nucleic acid is immunologically cross reactive with the polypeptide encoded by the second nucleic acid. Thus, a polypeptide is typically substantially identical to a second polypeptide, for example, where the two peptides differ only by conservative substitutions. These polypeptide sequence comparisons are enabled by the Smith-Waterman, HMM and EMotif algorithms.

As is well known to one of ordinary skill in the art, results from a homology search or analysis includes: a plurality of cDNA query sequences; a list of homologous (target) sequences; an E-Value that describes the probability that the original (query) sequence match with the target sequence could occur randomly; the annotation of the target sequence, if provided; an alignment of the query sequence to each target sequence; the percent identity of the query sequence to the target sequence; the hit length, or length of the sequence over which the percent identity is determined.

Figure 4:
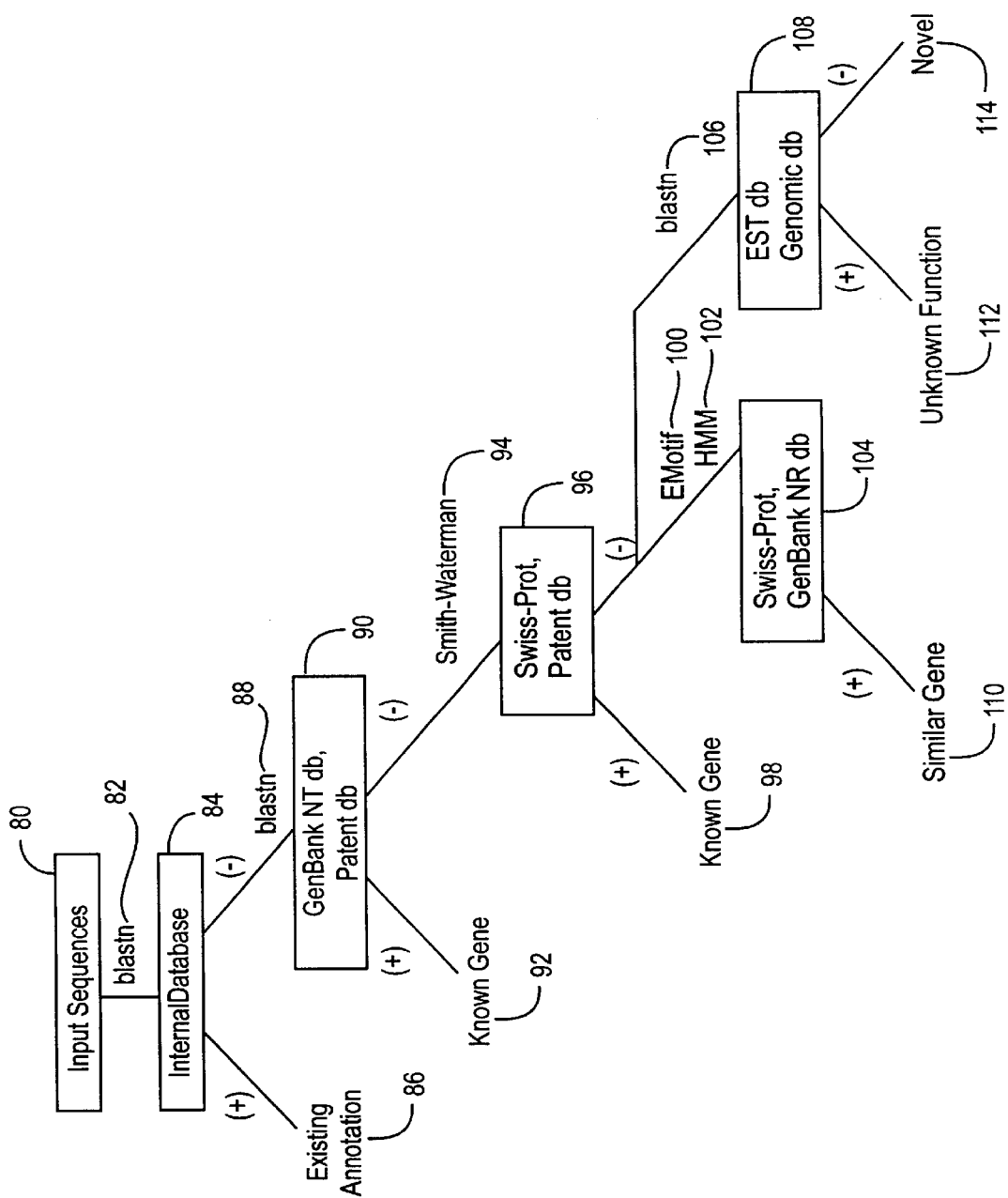
FIG. 4 depicts a process of performing homology analysis for a plurality of sequences according to an embodiment of the present invention.

The complete homology analysis of a plurality of sequences according to an embodiment of the present invention is composed of a process described in FIG. 4. The output(s) from the process shown in FIG. 4 may be used as the input to step 52 in FIG. 3. The rationale for this sequential strategy of homology analysis is to automate the method of sequence classification. According to the embodiment shown in FIG. 4, input sequences 80 are subjected to BLAST analysis 82 against an internal database of cDNA sequences 84. Near identical homologs (E-value<le-80) are sieved and recorded as being strong homologs of previously classified entries 86 of the internal database. Those sequences failing this test, are subjected to blastn analysis 88 against the GenBank nucleotide (NT) and patent databases 90. Those sequences showing strong similarity (E-value<le-50 with sequence length>200 nucleotides, 80% identity over 70% of the query sequence length) are classified as "known" genes 92. Those sequences failing this test are subjected to Smith-Waterman analysis 94 against the protein databases of Swiss-Prot and the translated patent database 96. Those sequences with E-values<le-20 with 80% identity over a segment length>50 amino acids are classified as "known" genes 98 while sequences with an E-value>le-20 are subjected in parallel to (a) HMM 102 and EMotif 100 analysis against the Swiss-Prot and GenBank non-redundant (NR) protein databases 104 and (b) BLASTN analysis 106 against the GenBank EST and genomic databases 108. Those sequences with an E-value<le-9 after HMM or EMotif are scored as "Similar" genes 110 while sequences with an E-value<le-60 after the final BLASTN analysis 106 are classified as "unknown" 112. Any sequences failing this last test, are classified as "Novel" 114.

Figure 7:
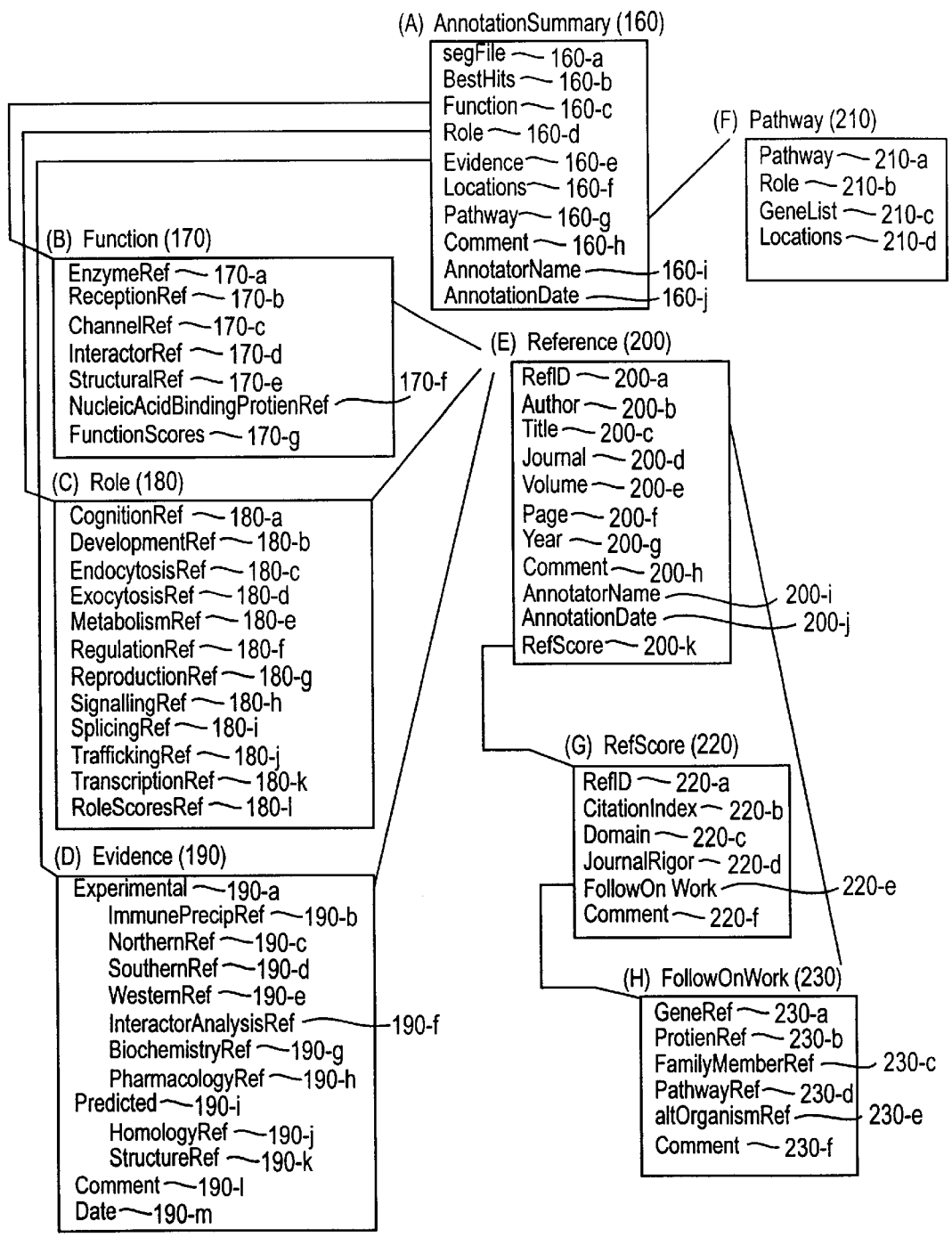
FIG. 7 depicts a database schema showing the functional annotative information stored for the genes according to an embodiment of the present invention.
Figure 8:
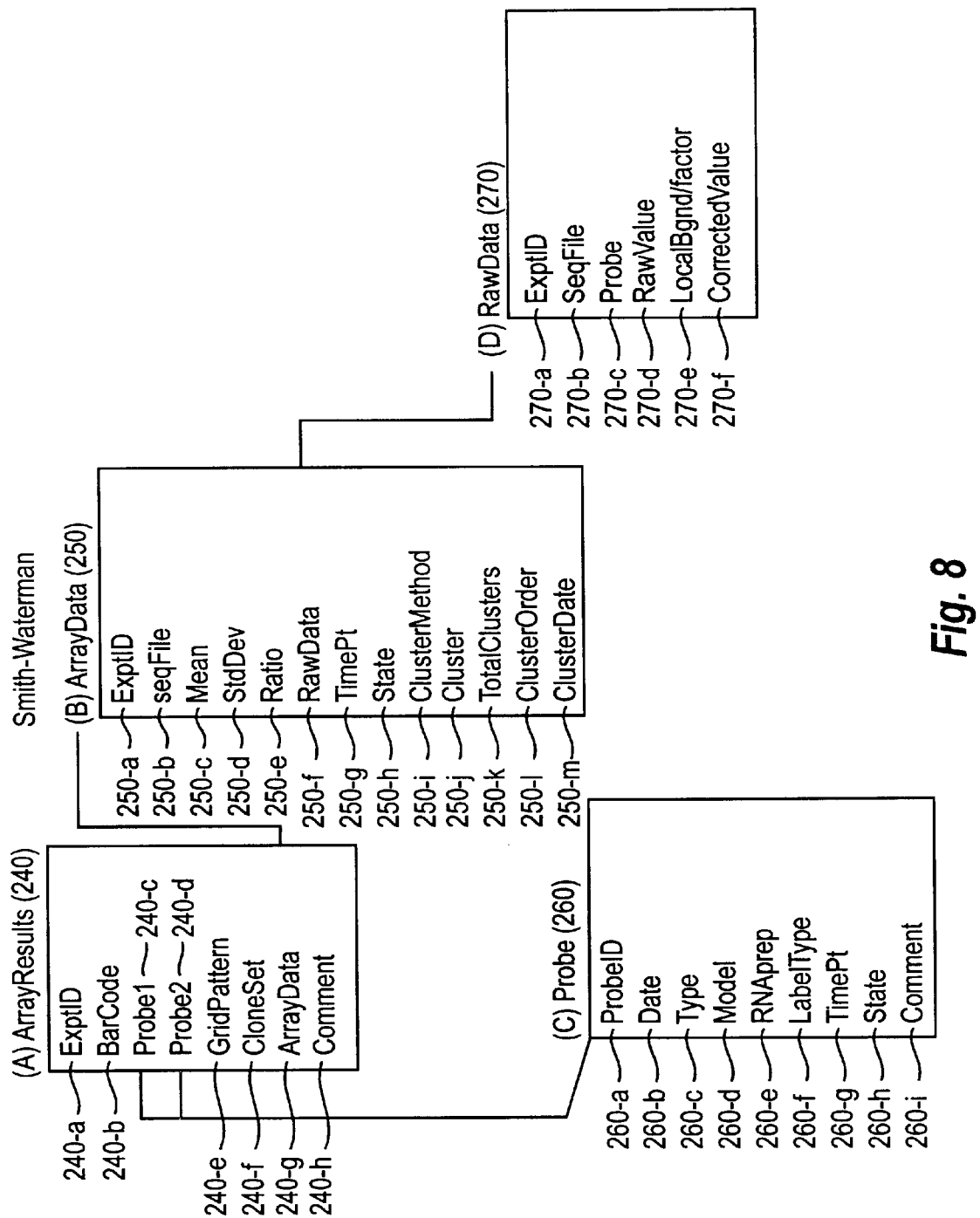
FIG. 8 depicts a database schema showing the gene expression profile data stored for the genes according to an embodiment of the present invention.

The present invention extracts relevant information from the homology analysis output as described above for each input DNA sequence, organizes the information, and stores it in a format which facilitates further processing and analysis of the information (step 54). According to an embodiment of the present invention, the information extracted from the BLAST, Smith-Waterman and HMM search output is stored in a database. The information extracted and stored by the present invention during step 54 is shown by the database schema depicted in FIG. 5. FIGS. 7 and 8 depict other database structures for storing information according to an embodiment of the present invention.

Figure 5:
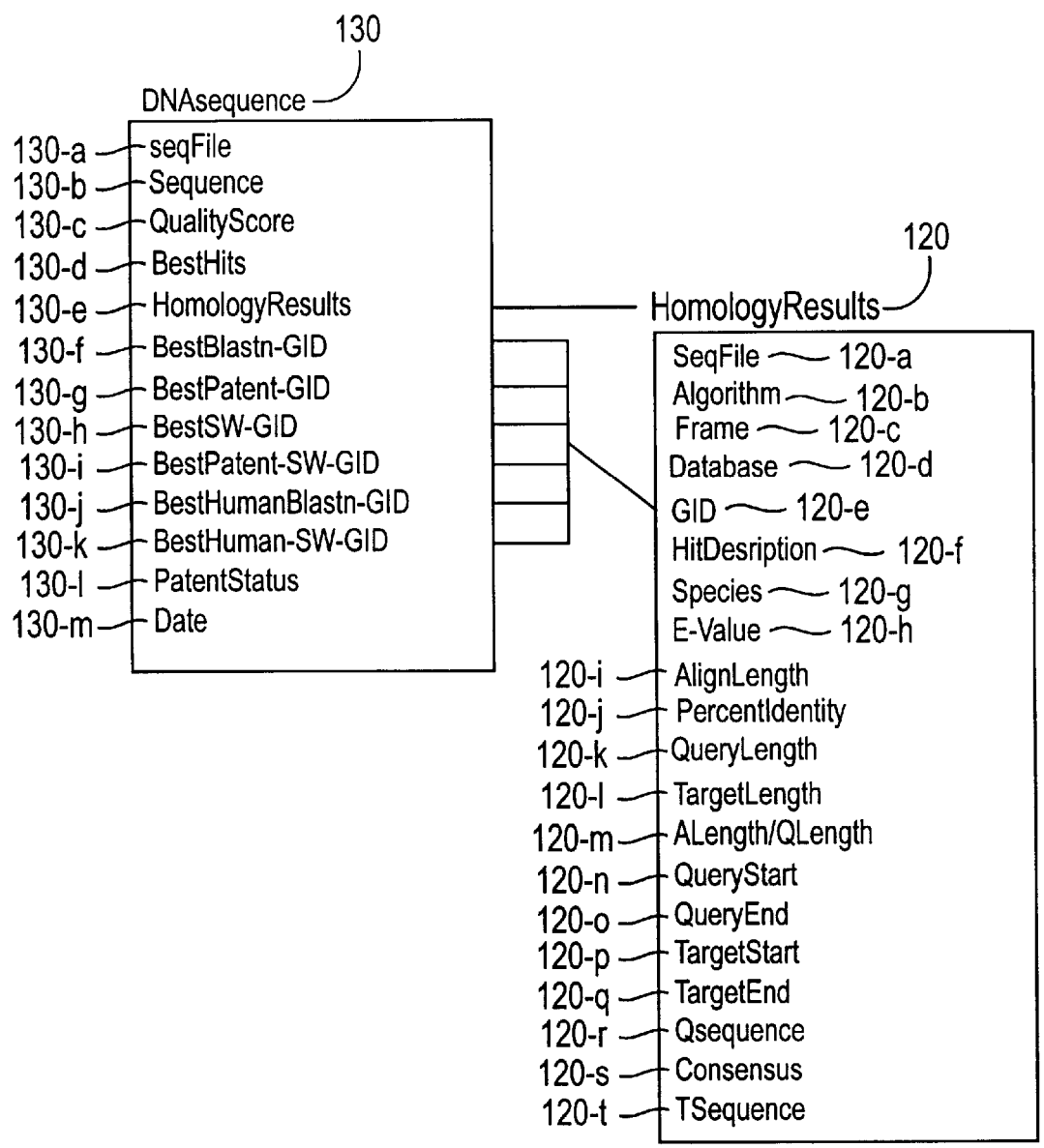
FIG. 5 depicts a database schema showing information extracted from homology search results and stored for the query cDNA sequences according to an embodiment of the present invention.

FIG. 5 shows information (database table "HomologyResults" 120) which is extracted from the homology search results, and stored for each query cDNA sequence according to an embodiment of the present invention. It is important to note that multiple (typically 10) homologs for each query sequence are stored in this database table in order to facilitate extraction of the most descriptive and accurate annotation for the query sequence. It should also be evident that various other formats, in addition to tables and databases, may also be used to store the information. The following scenario is common: the top 1, 2, 3, 4 or 5 blastn homologs of a query have E-values within a 10-fold range and are<le-50 yet lack informative annotative information (e.g. such homologs are expressed sequence tags or genomic DNA). However, the second, third, fourth, fifth, sixth or seventh homolog's E-values might have the following attributes: the E-value is less than le-50 and is within 10 or 100 fold of the top hit but the weaker homolog's annotation might provide more informative description of the query sequence's role or function; e.g. the weaker homolog might be an enzyme, receptor or structural protein. Identification of these more accurate descriptions are facilitated by a combination of keyword tables and information extraction methods described herein. In these circumstances, those of normal skill in the art of bioinformatics will recognize that the weaker hit provides the most useful annotation provided the E-value meets the above criteria.

For each homolog, the present invention stores, in database tables "DNAsequence" 130 and "HomologyResults" 120, the name of the sequence (attribute "seqFile" 130-a and 120-a), the sequence ("Sequence" 130-b), the quality scores or Phred values (Ewing, Hiller, Wendl & Green, Genome Research, 8:175–185, 1998), ("QualityScores" 130-c), the accession number of any homolog, i.e. the GenBank identifier number ("GID"120-e), the best GID derived from BLAST analysis ("BestBlastnGID" 130-f), the best GID derived from BLAST against the patent DNA database analysis ("BestPatent-GID" 130-g), the best GID derived from Smith-Waterman analysis derived from the Swiss-Prot database ("BestSW-GID" 130-h), the best GID derived from Smith-Waterman analysis of the patent (database "BestPatent-SW-GID" 130-i), the best GID derived from the best human homolog in BLAST analysis ("BestHumanBlastn-GID" 130-j), and the best GID derived from the best human homolog derived from Smith-Waterman analysis ("BestHuman-SW-GID" 130-k). For any homolog, the algorithm (e.g. BLAST or HMM) used for the homology search is recorded ("Algorithm" 120-b), the frame of the predicted protein for protein comparisons ("Frame" 120-c), the database searched ("Database" 120-d), the GenBank annotation for any homolog ("HitDescription" 120-f), the species of the annotation ("Species" 120-g), the E-value ("E-value" 120-h), the length of the alignment region ("AlignLength" 120-i), the percent identity of the aligned sequences ("PercentIdentity" 120-j), the length of the query in the alignment ("QueryLength" 120-k), the length of the target in the alignment ("TargetLength" 120-l), a number representing the fraction of the total query length represented in the hit region ("ALength/QLength" 120-m), the start position of the query sequence in the alignment ("QueryStart" 120-n), the position of the end of the query ("QueryEnd" 120-o), the start position of the target sequence ("TargetStart" 120-*p*), the end position of the target sequence ("TargetEnd" 120-*q*), the query sequence in the alignment ("QSequence" 120-*r*), the consensus of the alignment ("Consensus" FIG. 120-*s*), and the target sequence in the alignment ("TSequence" 120-*t*).

Figure 6:
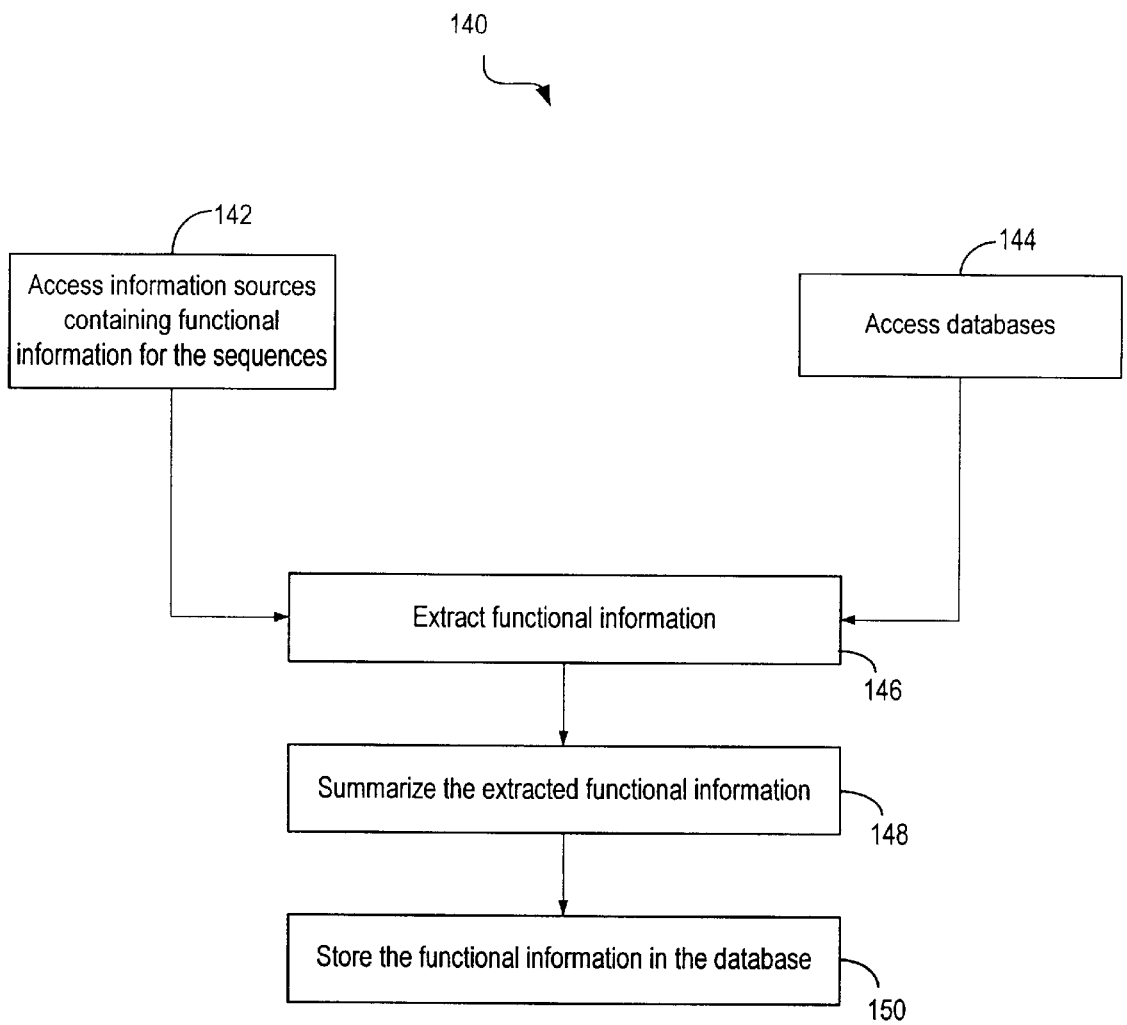
FIG. 6 is a simplified flowchart showing processing performed by an embodiment of the present invention for obtaining descriptive annotative information for the genes.

Referring back to FIG. 3, server 14 then obtains (step 56) descriptive annotative information on the biochemical function(s) and the physiological role(s) for the known genes from the plurality of cDNA sequences and stores the information in the database (step 58). FIG. 6 depicts a simplified flowchart 140 showing processing performed by an embodiment of the present invention for obtaining descriptive annotative information for the known genes. As shown in FIG. 6, several different techniques may be used by the present invention to obtain the functional information. According to a first technique, the present invention accesses information sources containing functional information related to the known genes (step 142). The information sources may include articles, published material, and other like material accessible to server 14. According to a specific embodiment, the present invention may use the accession numbers or the GenBank identifiers (GIDs) associated with the DNA sequences and their homologs to find the published material. Text processing tools may then be used by the present invention to automatically extract functional information from the information sources accessed in step 142 (step 146). The extracted information may then be summarized (step 148) and stored in the database (step 150).

According to another technique, the present invention may obtain the functional information from databases storing functional information and which are accessible to server 14 (step 144). Examples of such databases include databases provided by Proteome of Boston, Mass., DoubleTwist of Oakland, Calif., the Genbank database of deposited DNA and protein sequence data (http://www.ncbi.nlm.nih.gov:80/entrez/), the SWISS-PROT protein database (http:/www.expasy.ch/sprot/), the PubMed or Medline (NCBI) (http://www.ncbi.nlm.nih.gov) databases of abstracts derived from thousands of peer-reviewed biomedical journals, and other like databases. The Proteome databases are concise descriptions of known genes, their protein products and their functions and roles and known interactors as described in the current literature. The information extracted from the published material and genomic databases may then be summarized (step 148) and stored in the database (step 150).

The GenBank record of a cDNA or gene sequence commonly contains references to peer-reviewed publication information, stored in the Medline database about the gene. The Medline database can be accessed via the Internet via the PubMed interface (http://www.ncbi.nlm.nih.gov:80/entrez/query.fcgi). Alternatively, the GenBank record contains informative keywords related to the gene which may be used to perform broad topic searches on the Medline database. For example, protein products of genes participate in many processes essential to metabolism, development and reproduction. In some cases, a protein encoded by a gene may have more than one function and/or more than one role. For example, the yeast inositol 1-4-5 triphosphate kinase enzyme adds a phosphate moiety to phosphoinositol- an important component involved in signaling. However, this protein also can act as a regulatory scaffolding protein for transcription factors in the nucleus (Audrey R. et al. Science 287:2026–2029, 2000). Thus, this single protein can function as both an enzyme and a structural protein. Similarly, this gene product has two roles: it can participate in signaling processes and mRNA transcription. These instances are also examples of general pathways but further annotative information from the published literature could refine these topics to even more specific pathways. For example, the enzymatic activity might be most important for a growth hormone pathway and the structural role might be more important to a specific subset of transcription factors engaged in controlling cell division. In this invention, these relational links between genes and cellular or organismal processes constitute a web of interacting pathways that are extracted accurately and comprehensively.

The biological demands for information extraction from published material, such as abstracts, etc., in a comprehensive and consistent manner is unique to the world of manual biological annotation. Traditionally, extraction of information was done manually with varying degrees of consistency and accuracy. With recent advances in information extraction technologies, various software programs have been developed to automate information extraction and to summarize the extracted information. Examples of such programs include programs provided by Inxight Corp. of Santa Clara, Calif. Another example of a software package for information or knowledge extraction is the Crystal-Badger-Marmot suite from the Center for Intelligent Information Retrieval, Univ. of Massachusetts, Amherst, Mass. Such software programs have been applied to extract information from abstracts of published papers as well as from full-text papers. According to an embodiment of the present invention, these techniques are applied to generate tables of genes, tables of pathways composed of genes, and tables of relationships between and amongst genes and pathways. As described below, the validation of a relationship between or amongst genes is evaluated in a quantitative fashion.

According to an embodiment of the present invention, information extraction programs, such as those discussed above and others, may be used to extract (step 146 in FIG. 6) descriptive annotation information from information accessible to server 14 and to summarize (step 148 in FIG. 6) the information. According to an aspect of the present invention, the annotative information is stored in a database.

According to the present invention, information is extracted and stored for both the majority views and potentially multiple minority views. This is due to dramatic shifts in the understanding of biological systems over time. These shifts are also referred to as "paradigm shifts" (Kuhn, T., The Structure of Scientific Revolutions, Univ. Chicago Press 1962). According to these paradigm shifts, a minority view becomes accepted as being the correct interpretation after critical new data is acquired. The change in accepted "truth" of a paradigm can be dramatic or subtle in various domains of knowledge, and in the realm of biology both extremes can occur—hence the need for comprehensive collections of entity-relationships amongst genes, functions, roles and pathways. The need for storing both the majority and minority views becomes important when one realizes that the laws of biology are not yet deterministically known. This is substantially different from prior art bioinformatics techniques which only stored information related to the majority view (e.g. T. Rindflesch, L. Tanabe, J. Weinstein & L. Hunter PSB 2000:517–528).

For example, for a given biological topic, perhaps 51, 75, or 90 out of 100 published abstracts may describe a phenomenon as being caused by the interactions of genes A and B whereas a smaller subset of abstracts, perhaps 10, 25 or 49 may describe a more complex interaction between genes A and C prior to gene B. The former A-B model would be considered the consensus, "majority view" model (a "truth") and the latter A-C-B model would be considered a "minority view" and likely regarded as being "false." According to traditional bioinformatics techniques, only information related to strict "truths" was maintained and information related to the minority view(s) was discarded to reduce the amount of data being stored.

According to an embodiment of the present invention, minority views (e.g. unusual or unexpected relationships between genes or metabolic pathways) are also stored in the database but assigned a lower reference score (see "RefScore" attribute 200-k in table "Reference" 200 in FIG. 7, "FunctionScores" attribute 170-g in table "Function" 170, "RoleScores" attribute 180-l in table "Role" 180, and attributes 220-a through 220-f of table "RefScore" 220.) associated with the descriptive annotation of the known genes from the plurality of cDNA. The reference score (or their summary scores, "FunctionScores" 170-g and "RoleScores" 180-l) quantizes the "acceptance/majority opinion" for an alleged role or function of a gene. Of particular importance to "minority" views is the extraction and recording of special circumstances or boundary conditions under which the phenomena or relationship amongst genes might exist. For example, information related to minority views (e.g. unusual or unexpected relationships between genes or metabolic pathways) is stored in the database but assigned a lower reference score than information associated with the majority view. The metric for evaluating a specific published reference article also assigns a score derived from the Citation Index database (Institute for Science Information, Philadelphia) which quantitatively ranks the impact of a given paper by the number of times that paper is subsequently referenced. For the most significant papers, a published article can be referenced thousands of times. The Citation Index also ranks journals with high impact but only from the same criteria of frequently-cited papers from the journals regardless of whether the published paper is ultimately revised or shown to be inaccurate or limited to a set of conditions. Hence, one embodiment of this invention provides a mechanism to take into account the quality of the information source. This is both general and a specific measure. In general, articles in journals respected by a consensus of biomedical and genomics practitioners are believed to be reliable. For example, a publication in journals with a recognized, rigorous peer-review process (e.g. Science, Nature, the Journal of Biological Chemistry, or the Journal of Clinical Investigations) would receive 100 points or >90 points whereas publication in "lesser" journals (e.g. Journal of Antisense Research or Experimental Cell Research) would only receive 10 or 40 points.

FIG. 9 is an exemplary look-up table for general rankings of such biomedical journals. However, scores from FIG. 9 may be adjusted because the information source's peer-review process can be dependent upon the reviewers for a given domain or the degree of democratic consensus of a journal's editorial board. A domain specific weighting factor is derived for the major journals and can be applied systematically while in other cases, a human annotator must make the judgment. The adjustment can range between 10 and 50% of the original score and an article in a "lower-quality" journal can be upgraded or an article in a "higher-quality" journal can be downgraded.

While subject to a degree of subjectivity, these standards for ranking journals and their domain preferences are the same as those used by faculty-tenure review committee in major medical schools in the United States of America in order to evaluate the publication record of a tenure-candidate. Similarly, human experts in various domains recognize that certain information sources can have a predisposition to disregard or highly regard certain authors or types of submitted work. Since the editorial board and peer-reviewers of journals change with time, the tables for grading journals are not static but must be revised over time as reviewers or editors specific to domain specialties change. In combination with the Citation Index of impact journals, these criteria enable the scoring of a reference's support of gene's annotation.

Another variable used in the evaluation of the experimental support for an alleged role or function for a gene is a "follow-on" parameter. Reliable experimentalists often will publish a series of papers in reputable journals. They may publish on the same gene or encoded protein ("GeneRef" 230-a attribute of table "FollowOnWork" 230 in FIG. 7, or "ProteinRef" 230-b), a close homolog ("FamilyMemberRef" 230-c), another gene in the same pathway ("PathwayRef" 230-d) or the same gene or pathway in another organism ("altOrganismRef" 230-e). When a large body of work from an individual author or group of authors accumulates, then the probability of "truth" is high. In contrast, a single publication by an author that alleges unusual relationships amongst genes that fails to engender follow-on work (as roughly measured by the Citation Index) by the original author or others has a lower probability of "truth" which is reflected by a lower reference score ("RefScore" 200-k). An intermediate reference score occurs where a single publication triggers much work by other investigators, e.g. a high Citation Index but low "follow-on" value. Thus, this strategy compensates for the overall weakness of the Citation Index—by merely enumerating the occurrences of a referenced paper, the Citation Index may not be accurately represent the relatedness of subsequent work.

FIG. 7 depicts the functional annotative information stored for the genes according to an embodiment of the present invention. Database tables 160, 170, 180, 190, 200, 210, 220, and 230 depicted in FIG. 7 include annotation information derived from peer-reviewed articles and other information accessed by server 14. A table of the annotation summary ("AnnotationSummary" 160) includes the sequence name ("SeqFile" 160-a), best hits ("BestHits" 160-b) which refers to the "DNAsequence" table 130 ("BestBlastnGID" 130-f), a link to the "Function" table 170 ("Function" 160-c), a link to the "Role" table 180 ("Role" 160-d), a link to the "Evidence" table 190 ("Evidence" 160-e). The Function 170, Role 180 and Evidence 190 tables contain many attributes which all refer to individual References ("Reference" table 200). Any reference in "Reference" table 200 ("RefID" 200-a) that supports the concept that a gene is an enzyme ("EnzymeRef" 170-a), a receptor ("ReceptorRef" 170-b), a channel or transporter ("ChannelRef" 170-c), a protein interactor ("InteractorRef" 170-d), a structural protein ("StructuralRef" 170-e), a nucleic acid binding protein ("NucleicAcidBindingProtein" 170-f), has a role in cognition ("CognitionRef" 180-a), or a role in development ("DevelopmentRef" 180-b), or a role in endocytosis ("EndocytosisRef" 180-c), a role in exocytosis ("ExocytosisRef" 180-d), or a role in Metabolism ("MetabolismRef" 180-e), or a role in regulation ("RegulationRef" 180-f), or a role in reproduction ("ReproductionRef" 180-g), or a role in signaling ("SignallingRef" 180-h), or a role in RNA splicing ("SplicingRef" 180-i), or a role in vesicle trafficking ("TraffickingRef" 180-j), or a role in transcription ("TranscriptionRef" 180-k) is duly linked to the appropriate reference identifier ("RefID" 200-a). The weighted scores for each of these possible functions is stored as a multi-item list ("FunctionScores" 170-g). Similarly, the weighted scores for each of the possible roles is stored as a multi-item list; e.g. a "RoleScores" (180-l) equivalent to "0,100,100,0, 0,0,0,0,0,0,0" might correspond to a single published article on a gene's role in the endocytosis of key nutrients during development in a prominent journal such as Science ("DevelopmentRef" 180-b and "EndocytosisRef" 180-c). In a database query, such a summary weighted score can be simply compared to other scores by both the maximum value of each comma-delimited item as well as the rank order amongst comma-delimited items. Similarly, any experimental evidence contained in the reference that shows that a gene's encoded protein was immune precipitated ("ImmunePrecipRef" 190-b), a gene's encoded mRNA was hybridized in a Northern assay ("NorthernRef" 190-c), a gene was hybridized in a Southern blot ("SouthernRef" 190-d), a protein band of appropriate predicted size was identified in a Western blot ("WesternRef" 190-e), an open reading frame was identified in a yeast two-hybrid interactor analysis ("InteractorAnalysisRef" 190-f), an enzymatic assay ("BiochemistryRef" 190-g), a pharmacological profile was determined ("PharmacologyRef" 190-h), a predicted homologous domain ("HomologyRef" 190-j) or a predicted structural 3-dimensional motif ("StructureRef" 190-k) is duly referenced to the appropriate reference identifier ("RefID" 200-a).

Referring further to FIG. 7, tables are shown to record the information about any pathway or reference. For any pathway ("Pathway" 210-a in table "Pathway" 210), a role may be assigned ("Role" 210-b), genes of the pathway listed ("GeneList" 210-c) and the location of the pathway identified ("Locations" 210-d). For any reference, a unique identifier ("RefID" 200-a) is recorded, the authors listed ("Author" 200-b), the article title ("Title" 200-c), the journal in which the article was published ("Journal" 200-d), the volume of the journal ("Volume" 200-e), the page numbers of the article ("Page" 200-f), the year of the article's publication ("Year" 200-g), and the reference score link ("RefScore" 200-k). The reference score link 200-k corresponds to the "RefScore" object/table 220 which also contains the reference identifier ("RefID" 220-a), the citation index value (if any) ("CitationIndex" 220-b), the topic field (e.g. immunology or neurobiology) ("Domain" 220-c), a domain weight-adjusted value for the journal quality, as described above, ("JournalRigor" 220-d), and the link to follow-on work table 230 ("FollowOnWork" 220-e). The follow-on table 230 consists of a reference to any subsequent work in which the same gene ("GeneRef" 230-a)or protein ("ProteinRef" 230-b), or homologous gene ("FamilyMemberRef" 230-c), or the same pathway ("PathwayRef" 230-d) or alternate organism ("altOrganismRef" 230-e) was studied by the original investigators.

Referring back to FIG. 3, the present invention then obtains (step 59) and stores (step 60) expression profile data for the genes and their homologs. The expression profile data for a gene describes how the gene is expressed, or transcribed to RNA. Profiles can be created for genes in cells or tissues under influences of a drug, as a cell or tissue develops, or during changes to the physiological state of the cell or tissue, or in response to the development of disease in humans or an animal model. For example, the expression profile data may indicate whether a gene is up-regulated/down-regulated during a stroke.

FIG. 8 depicts the gene expression profile data stored in the database according to an embodiment of the present invention. The four tables depicted in FIG. 8 correspond to a summary of the array result conditions ("ArrayResults" 240), the summarized array data ("ArrayData" 250), the details of the probe(s) ("Probe" 260), and the raw data ("RawData" 270). The array result conditions table 240 contains attributes that describe a unique experimental identifier ("ExptID" 240-a), the corresponding bar code ("BarCode" 240-b), the link for probe 1 ("Probe1" 240-c), the link for probe 2 ("Probe2" 240-d), a term that describes the grid pattern ("GridPattern" 240-e), the clone set identifier ("CloneSet" 240-f), the link to array data ("ArrayData" 240-g), and a comment ("Comment" 240-h). The array data table 250 contains attributes to describe the experimental identifier ("ExptID" 250-a), the name of the cDNA sequence ("seqFile" 250-b), the arithmetic mean of the background or normalized data ("Mean" 250-c), the standard deviation ("StdDev" 250-d), the ratio of any paired means derived from simultaneous application of two probes ("Ratio" 250-e), the time point at which the probes were made ("TimePt" 250-g), the biological state (e.g. diseased or normal) of the probe's mRNA origin ("State" 250-h), the clustering method ("ClusterMethod" 250-i), the cluster number ("Cluster" 250-j), the total number of clusters ("TotalClusters" 250-k), the cluster order pattern derived from the auto-regression analysis used in the causality analysis ("ClusterOrder" 250-l) and the date of the clustering ("ClusterDate" 250-m).

The probe data table 260 contains attributes for the probe identifier ("ProbeID" 260-a), the date of probe generation ("Date" 260-b), the type (first strand cDNA or double-stranded cDNA) of probe ("Type" 260-c), the biological model ("Model" 260-d), the identifier for the preparation of RNA ("RNAprep" 26-e), the labeling (radioactive or fluorescent) method ("LabelType" 260-f), the time point at which the RNA was collected ("TimePt" 250-g), the biological state of the probe's mRNA origin ("State" 250-h), and a comment ("Comment" 260-i).

The raw data table 270 contains attributes for the experimental identifier ("ExptID" 270-a), the sequence name ("seqFile" 270-b), the probe name ("Probe" 270-c), the raw intensity value ("RawValue" 270-d), the local background or normalization factor ("LocalBgnd/factor" 270-e), and the arithmetically corrected intensity value ("CorrectedValue" 270-f).

Referring back to FIG. 3, the present invention then performs clustering analysis on the behavior of DNA sequences in expression profile studies (step 62). According to clustering analysis, data complexity is reduced by partitioning the genes into groups or "clusters" that have similar attributes. These attributes can be the behavior of genes monitored over multiple time points in response to an injury, onset of disease or altered physiological state (e.g. intensity or ratio of intensities resulting from hybridization of a gene set with probes derived from normal and diseased tissue). Also, these attributes can simply be the response of genes from cells, tissues or animals treated with multiple concentrations (e.g. 5, 6 or 7 concentrations) of many drugs (e.g. 10, 100, 1000 or 10,000) with differing mechanisms of action at a single time point. These attributes can also be the response of cells or animals subjected to many altered physiological states (e.g. elevated or diminished nutrients, ions or temperature, transient ischemia, shock, anxiety, discomfort or depression) monitored at a single time point relative to untreated cells or tissues. The result of clustering gene expression data are clusters of genes with similar expression profiles.

An embodiment of the present invention implements a method of gene clustering that is tuned to the simplified, yet specific nature of the array data itself. In order to reduce data complexity, many clustering methods have been applied to gene expression profile data: these include hierarchical, K-means, self-organizing maps (Tamayo et al. PNAS 96:2907–12), or support vector machines (M. Brown et al. PNAS 97:262–7). An embodiment of the present invention uses a K-means distance with Euclidean distance or other distance metrics (provided by Partek of St. Louis Mo.) because of its ability to efficiently cluster data in an automated unsupervised manner. One of the common criticisms of K-means clustering is that the number of clusters must be determined a priori. However, the present invention uses the Davies-Bouldin algorithm (IEEE Transactions on Pattern Analysis and Machine Intelligence, Vol. PAM1-1, April 1979) which determines the optimal number of clusters based upon the dispersion and flatness of clusters.

According to an embodiment of the present invention, the present invention may cluster the genes based on time-course data as described by the expression profile data. According to a specific embodiment of the present invention, packages provided by Partek Inc. and/or SAS Institute, Incorporated of Cary, N.C. may be used to perform the clustering analysis. For time-course data, the clustering analysis may also include causality analysis to predict ordered relationships between clusters on a time basis. Causality analysis is performed using a regressive method performed with software packages such as the Statistical Analysis Software from SAS Institute, Incorporated. The results from the clustering analysis are stored in a database (step 64). The cluster analysis results are inserted into the array data table 250 of FIG. 8: for each gene ("seqFile" 250-*b*), the clustering method ("ClusterMethod" 250-*i*), a cluster number ("Cluster" 250-*j*), the total number of clusters ("TotalClusters" 250-*k*), and the cluster order ("ClusterOrder" 250-*l*).

The type of clustering method(s) used to analyze array data depends upon (a) a priori knowledge about the behavior of the immobilized genes, (b) the composition of the gene set itself, and (c) the choice of array technologies. Array technologies come in two general forms: cDNA and oligo-nucleotide arrays. Since the Affymetrix arrays often have a higher density than cDNA arrays, the emphasis has been to increase the number of sequences per unit surface area in order to gain thoroughness. Often times, inadequate attention is paid to the design of the actual DNA attached to the array. Thus, many array chip designs seek to deposit large numbers of gene fragments per chip; such as species-specific chips (mouse, rat or human chips from Affymetrix, Santa Clara, Calif.) or genes representative of a field (apoptosis, cancer or neurobiology chips from Affymetrix or Clonetech, Palo Alto, Calif. However, analysis of such chips is complicated by the fact that most genes on the chip may be irrelevant to the biological system being studied.

According to the present invention, the analysis of gene clusters is vastly simplified by the immobilization of a plurality of genes that are actually disease- or physiologically-specific. Such collections of genes can be generated by any method that enables the identification of genes expressed at a measurable level higher in one state than another. For example, in tumors or animals subjected to ischemia, those skilled in the art of molecular cloning can identify and isolate cDNA clones and derive the sequences thereof for genes whose expression is elevated 2, 3 or 10 fold higher in the altered physiological state; e.g. differential display and subtractive cloning are two such methods. The number of disease-related or physiologically-related genes may range from 1000, 6000, 10,000, or 20,000 per chip.

When analyzed by principal components analysis, typically 90% of the variability in the gene expression profile data generated by arrays of 6000–10,000 disease- or paradigm-specific cDNA targets can be explained by the first 3 principal components or eigenvectors. With a large number of genes unrelated to the biological paradigm of the probe (e.g. 40,000–60,000 genes present on some Affymetrix arrays), the data variability is likely explained by many more principal components which makes it difficult to analyze more than any 3 of all principal components in 3-dimensional space. For these instances, other clustering methods might be more appropriate, such as hierarchical clustering. However, optimal hierarchical clustering is highly iterative and false clusters are often generated.

In order to infer the time-order of gene clusters derived from the above, it is possible to calculate likely causality by a moving auto-regressive analysis. A time-order is a linear ranking of clusters by a deduced set of relationships ordering the first possible cluster relative to other clusters in an iterative process. A biological example of this problem is the goal of understanding which genes respond earliest to an injury or infection followed by the elucidation of time of activation of subsequent, related or unrelated genes. A ordered set of clusters from expression profile data is achieved initially by selecting a representative subset of genes near the centroid of each cluster (e.g. 2, 5 or 10 representing 1–10% of the total number of genes) and performing a moving auto-regressive test against the remaining genes of the monitored population of genes (e.g. 2, 5 or 10 genes compared to all 6000 or 10,000 genes) from all clusters (Statistical Analysis Software of SAS Institute, Incorporated, Cary, N.C.). The ranked order of clusters is stored in "ClusterOrder" (250*l*) in step 64.

The accuracy of ordering clusters is dependent on the completeness of the calculation, but calculation of cluster order is computationally intensive. For example, according to a specific embodiment, the above calculation requires about 24 hours on a standard single CPU Unix workstation with 1 gigabyte of RAM; e.g. a Sun Ultra10 workstation with 300 MHz CPU. This time-series analysis is only applicable to datasets with regularly spaced time-points (e.g. 10, 20 or 40 instances spaced 30 min, 1 hr or 3 hrs apart). The time-resolution of the causality analysis is dependent upon the density of intervals over the entire course experimental course. For the highest resolution of time-ordered relationships amongst clusters, 20, 50, or 100 time-points are preferable. For the highest accuracy amongst clusters, a comprehensive auto-regression is calculated provided sufficient computer power (e.g. 6000 genes compared to 6000 genes or 10,000 genes compared to 10,000 genes requires supercomputer ability or the efforts of a cluster of workstations such as Beowulf: (http://www.beowulf.org/)).

Referring back to FIG. 3, after the clustering analysis, the present invention may obtain pathway information (step 65) for the genes and their homologs and store the pathway information to the database (step 66). Pathway information can be accessed from public pathway databases such as the Kyoto Encyclopedia of Genes and Genomes (KEGG) or the Munich Information Center for Protein Sequences (MIPS), or derived from the literature using information extraction methods, as described earlier.

According to an embodiment of the present invention, the database used for storing information associated with the genes correlates the annotative information with numerical gene expression profile data. Within each time-resolved cluster of genes with similar behavior, multiple types of genes may exist ("Cluster" 250-*j* is linked to "seqFile" 250-*b* which can be referenced to the annotation summary "seqFile" 160-*a*). For example, genes that are stimulated immediately after an injury or stress might include chaperones or heat shock proteins in order to prevent misfolded proteins. Similarly, transcription factors might be triggered to increase the production of protective systems. All of these genes' mRNA levels could be elevated within the first 5 minutes post-injury but their mRNA levels might diminish at varying rates. Subsequently, secondary and tertiary groups of genes might be activated in response to the transcription factors. While the clustering and causality analysis described above can identify groups of early onset genes, it cannot distinguish the functional relationship, if any, between differing kinds of genes within each time-ordered group. For this task, integration of the annotation of all genes for each time-ordered group is necessary. Currently, such analyses are performed by human experts and are limited by recall while a database query constrained by user-defined parameters could present all possible cross-connections that are likely or less likely—depending upon the reliability threshold ("FunctionScores" 170-g, "RoleScores" 180-l) for "truth" of a relationship defined by the user. Thus, multiple alternate scenarios can be presented in a database or in tabular form or graphical objects linked by lines that purport directional control and annotative text describing the likelihood of the interaction along with hyperlinks to relevant published articles via HTML (hypertext markup language) methods.

A feature of the present invention is that it provides support for both intra- and inter- time-resolved gene cluster components; i.e. between or amongst genes in subsequent or previous groups of genes. Thus, a human expert can choose from a palette of options to refine a first iteration of gene network or pathway building. The parameters in turn can be used to recalculate the likelihood of other annotations and pathways to explain the behavior of a single gene, group of genes, or cluster of genes. Collectively, these methods can reduce the number of differentially regulated genes to a smaller plurality; from which candidate genes can be chosen by the human expert.

The information stored in the database according to the present invention facilitates the identification of candidate genes (step 68 in FIG. 3). Identification of candidate genes results from the merge of the time-ordered gene expression clusters and the function(s), role(s) and/or pathway(s) information of the cluster members. The reference score-based assignments for either majority or minority view annotations of function(s), role(s) and/or pathway(s) enables the identification of new or serendipitous relationships. Such biological novelty, i.e. the unexpected up- or down-regulation of a gene in the context of an existing or new pathway, is one of the hallmarks of candidate genes. For example, in a signaling pathway, study of a disease model may reveal that one, two or three known phosphodiesterases are up-regulated in the context of a pathway not normally characterized by those enzymes. Or, a new family member of this enzyme class might be discovered up-regulated along with the expected enzyme. Both are examples of candidate genes revealed by the combination of annotated DNA sequences and expression profiling data—particularly if the published literature contained an obscure reference to such a relationship under abnormal circumstances dissimilar to the conditions of the experimental paradigm. The latter result would be significant due to the redundancy of biological systems. Conversely, if 7, 8 or 9 of 10 genes of a well known pathway are found to be up-regulated in a disease or injury model (as determined by a comparison of all pathways of each gene expression profile cluster), then the 1, 2 or 3 genes that failed to be induced (as determined by a query comparison to the pathway database) might also be considered candidate genes. In this example, the user might conclude that a new inhibitor is blocking the 1, 2, or 3 missing genes and hence blocking the inhibitor might diminish the pathology or improve recovery. The user might then search for known or postulated inhibitors of any member of the pathway.

The information stored in the database may be accessed or queried by users interested in identifying candidate genes. According to a specific embodiment, the present invention provides an interface allowing users to specify a query including criteria characterizing candidate genes. In response to the user query, the present invention searches the database to identify genes which satisfy the user-specified search criteria. A typical search might examine the group of classified genes (e.g. by function, role or pathway) appearing in an early or middle expression cluster (based on "Cluster" 250-j and "ClusterOrder" 250-1). By comparing the similar attributes (e.g. a query of the type "what apoptotic regulator genes are present in early clusters along chemokine genes?") within upstream or downstream clusters, the user may be able to deduce, for example, that the apoptotic pathway in a particular infection model of immune cells was altered by either (a) the appearance of a new apoptotic regulator gene or chemokine at an unexpected time or cluster, or (b) the absence of altered expression a gene known to be induced in the pathway. Alternatively, the user might query what low-likelihood roles or pathways might explain the presence of a given class of receptors. In response to the user query, the present invention uses the user-specified query criteria to search the information stored in the database and outputs genes which satisfy the user-specified search criteria by either their presence or omission from either known or low-likelihood roles (or pathways) or lists of genes with known function(s) or role(s). In this manner, the information stored for the plurality of DNA sequences and their behavior in expression profile data facilitates identification of candidate genes.

Although specific embodiments of the invention have been described, various modifications, alterations, alternative constructions, and equivalents are also encompassed within the scope of this application. The described invention is not restricted to operation within certain specific data processing environments, but is free to operate within a plurality of data processing environments. For example, although the present invention has been described in a distributed computer network environment, the present invention may also be incorporated in a single stand-alone computer system. In such an environment, the same stand-alone computer has access to the various biological databases according to the present invention and may act both as a client and a server. Additionally, although the present invention has been described using a particular series of transactions and steps, it should be apparent to those skilled in the art that the scope of the present invention is not limited to the described series of transactions and steps.

Further, while the present invention has been described using a particular combination of hardware and software, it should be recognized that other combinations of hardware and software are also within the scope of the present invention. The present invention may be implemented only in hardware or only in software or using combinations thereof.

The specification and drawings are, accordingly, to be regarded in an illustrative rather than a restrictive sense. It will, however, be evident that additions, subtractions, deletions, and other modifications and changes may be made thereunto without departing from the broader spirit and scope of the invention as set forth in the claims.

What is claimed is:

1. In a computer system, a method of identifying candidate genes from a plurality of DNA sequences, the method comprising:

obtaining results of a homology search for a first plurality of DNA sequences, the homology search results comprising information about homologs of the first plurality of DNA sequences;

obtaining annotative information for the first plurality of DNA sequences, the annotative information comprising information about biochemical functions and physiological roles of the first plurality of DNA sequences, wherein obtaining the annotative information comprises:

identifying one or more known genes from the first plurality of DNA sequences based on the homology search results, wherein a DNA sequence from the first plurality of DNA sequences is identified as a known gene if a sequence identity of the DNA sequence to a sequence stored in a first database of sequences used for the homology search is at least equal to a first threshold value;

accessing one or more information sources storing annotative information for DNA sequence;

extracting annotative information from the one or more information sources for the known genes, the extracted annotative information comprising information about one or more biochemical functions and physiological roles of each known gene; and assigning a reference score to the extracted annotative information for each known gene based on the level of acceptance of the roles or functions of the known gene as described by the annotative information such that annotative information with a high level of acceptance is assigned a higher reference score than annotative information with a low level of acceptance;

obtaining gene expression profile data for the first plurality of DNA sequences, the gene expression profile data describing behavioral patterns of the first plurality of DNA sequences;

clustering the first plurality of DNA sequences based on the behavioral patterns of the first plurality of DNA sequences as described by the gene expression profile data;

storing the results of the homology search, the annotative information, the reference score assigned to the extracted annotative information for each known gene, the gene expression profile data, and results from clustering the first plurality of DNA sequences in a database;

receiving a query identifying criteria for the candidate genes; and searching the database, in response to the query, to identify a set of DNA sequences from the first plurality of DNA sequences which satisfy the query criteria.

2. The method of claim 1 wherein the homology search for the first plurality of DNA sequences comprises performing BLAST analysis, Smith-Waterman analysis, Hidden Markov Model (HMM) analysis, and EMotif analysis.

3. The method of claim 2 wherein performing the BLAST analysis, the Smith-Waterman analysis, the Hidden Markov Model (HMM) analysis, and the EMotif analysis comprises:

performing the BLAST analysis on the first plurality of DNA sequences using the first database of sequences;

identifying a second plurality of DNA sequences from the first plurality of sequences based on the BLAST analysis, wherein a DNA sequence from the first plurality of DNA sequences is included in the second plurality of DNA sequences if a sequence identity of the DNA sequence to a sequence stored in the first database of sequences is less than a second threshold value;

performing Smith-Waterman analysis on the second plurality of DNA sequences using a protein database and a translated patent database;

identifying a third plurality of DNA sequences from the second plurality of sequences based on the Smith-Waterman analysis, wherein a DNA sequence from the second plurality of DNA sequences is included in the third plurality of DNA sequences if a sequence identity of the DNA sequence to a sequence stored in the first database of sequences is less than a third threshold value;

performing Hidden Markov Model (HMM) analysis and EMotif analysis on the third plurality of DNA sequences using the protein database and GenBank database; and performing BLAST analysis on the third plurality of DNA sequences using GenBank EST database.

4. The method of claim 1 wherein the one or more information sources include Genbank database, SWISS-PROT database, Medline database, and biomedical publications.

5. The method of claim 1 wherein:

accessing the one or more information sources comprises accessing biomedical publications;

assigning the reference score to the extracted annotative information for each known gene comprises:

for annotative information extracted from each biomedical publication:

assigning a reference score to the extracted annotative information based on characteristics of the biomedical publication, the reference score indicating the level of acceptance of the roles or functions of the known genes as described by the annotative information extracted from the biomedical publication.

6. The method of claim 5 wherein assigning the reference score comprises:

using a score derived from a citation index database to calculate the reference score, the score derived from the citation index database indicating the number of times that the annotative information from the biomedical publication was referenced by other information sources.

7. The method of claim 5 wherein assigning the reference score further comprises:

ranking the biomedical publications; and assigning the reference score to the annotative information extracted from the biomedical publication based on the ranking of the biomedical publication.

8. The method of claim 1 wherein clustering the first plurality of DNA sequences comprises determining relationships between clusters of DNA sequences from the first plurality of DNA sequences.

9. The method of claim 1 wherein clustering the first plurality of DNA sequences comprises clustering the first plurality of DNA sequences based on time-course data described by the gene expression profile data.

10. The method of claim 1 wherein storing the information in the database comprises correlating the annotative information for the first plurality of DNA sequences with the genes expression profile data for the first plurality of DNA sequences.

11. In a computer system, a method of identifying candidate genes comprising:

configuring a query identifying criteria for the candidate genes;

communicating the query to a server storing information related to a plurality of DNA sequences, the information comprising:

results of a homology search for the plurality of DNA sequences, the homology search results comprising information about homologs of the plurality of DNA sequences;

annotative information about the biochemical functions and physiological roles of the plurality of DNA sequences, wherein the annotative information is obtained by:

identifying known genes from the plurality of DNA sequences based on the homology search results, wherein a DNA sequence from the plurality of DNA sequences is identified as a known gene if a sequence identity of the DNA sequence to a sequence stored in a database of sequences used for the homology search is at least equal to a first threshold value; and accessing one or more information sources storing annotative information for DNA sequences;

extracting annotative information from the one or more information sources for the known genes, the extracted annotative information comprising information about one or more biochemical functions and physiological roles of each known gene; and assigning a reference score to the extracted annotative information for each known gene based on the level of acceptance of the roles or functions of the known gene as described by the annotative information such that annotative information with a high level of acceptance is assigned a higher reference score than annotative information with a low level of acceptance, wherein the annotative information stored by the server includes the reference score assigned to the extracted annotative information for each known gene;

information describing behavioral patterns of the plurality of DNA sequences; and results from clustering the plurality of DNA sequences based on the behavioral patterns of the plurality of DNA sequences as described by the gene expression profile data; and receiving from the server, in response to the query, a first set of DNA sequences from the plurality of DNA sequences, wherein the first set of DNA sequences satisfy the criteria for the candidate genes identified in the query.

* * * * *